Figure 1:
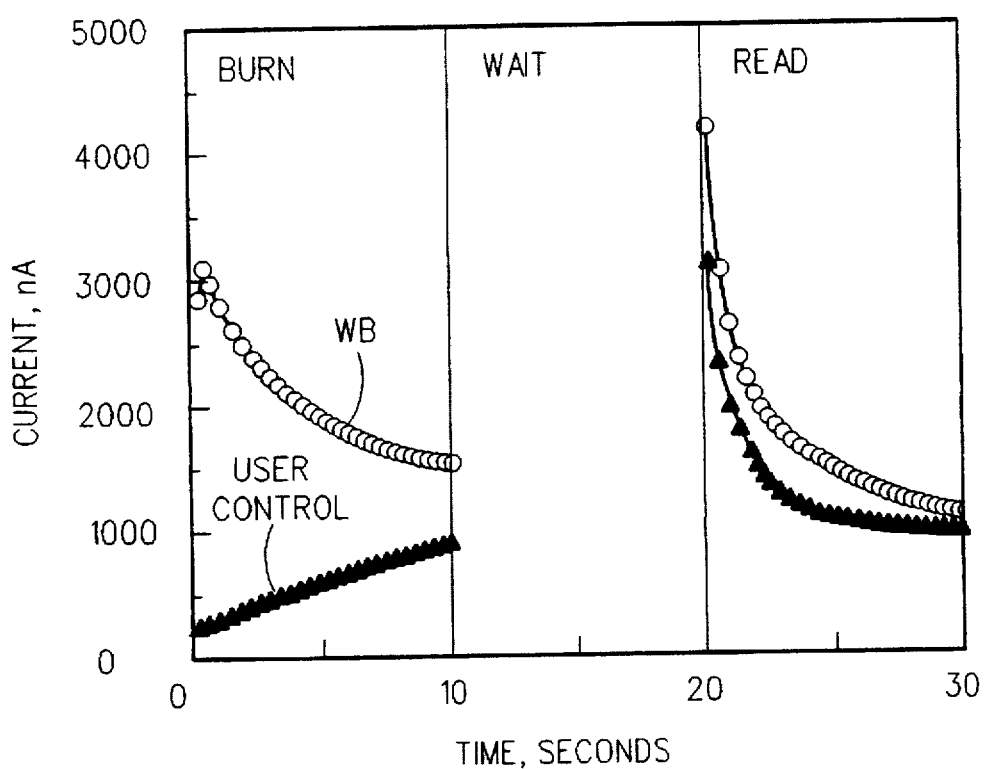

United States Patent [19]

Ye

[11] Patent Number: 5,723,284
[45] Date of Patent: Mar. 3, 1998

[54] CONTROL SOLUTION AND METHOD FOR TESTING THE PERFORMANCE OF AN ELECTROCHEMICAL DEVICE FOR DETERMINING THE CONCENTRATION OF AN ANALYTE IN BLOOD

[75] Inventor: Ling Ye, Mishawaka, Ind.

[73] Assignee: Bayer Corporation, Elkhart, Ind.

[21] Appl. No.: 625,132

[22] Filed: Apr. 1, 1996

[51] Int. Cl.$^6$ .............. C12Q 1/00; C12Q 1/54; A61M 1/14; C25D 5/00

[52] U.S. Cl. .............. 435/4; 435/14; 435/18; 435/25; 435/817; 435/2; 422/44; 422/50; 422/68.1; 205/81; 204/660; 204/193; 204/291; 436/63

[58] Field of Search .............. 435/4, 14, 18, 435/25, 817, 287, 2; 422/44, 50, 68.1; 205/81; 204/660, 193, 291; 436/63

[56] References Cited

FOREIGN PATENT DOCUMENTS

| 21928A | 4/1992 | WIPO . |
| 13535A | 11/1993 | WIPO . |
| 13536A | 11/1993 | WIPO . |

*Primary Examiner*—Louise Leary
*Attorney, Agent, or Firm*—Jerome L. Jeffers

[57] ABSTRACT

The present invention relates to a control solution for and a method of testing the performance of an electrochemical sensing device for determining the concentration of an analyte in a blood sample. The device contains a sensing means having a working electrode on which is deposited an enzyme capable of reacting with the analyte to provide electrons and a mediator to shuttle the electrons to the surface of the working electrode. The control solution is formulated so that the device will recognize the control solution as being something other than blood and automatically exclude the results obtained with the control solution from its memory unit.

18 Claims, 1 Drawing Sheet

CONTROL SOLUTION AND METHOD FOR TESTING THE PERFORMANCE OF AN ELECTROCHEMICAL DEVICE FOR DETERMINING THE CONCENTRATION OF AN ANALYTE IN BLOOD

BACKGROUND OF THE INVENTION

The field of clinical chemistry is concerned with the detection and quantification of various substances in body fluids. In one important aspect of this field, the concentration of naturally occurring substances, such as cholesterol or glucose, in an individual's blood is determined. One of the most frequently used analytical devices in clinical chemistry for a blood sample is the test strip. Upon contacting the test strip with the blood sample, certain reagents incorporated into the test strip react with the analyte to be determined to provide a detectable signal. The signal may be a change in color as in the case of a colorimetric sensor or a change in current when an electrochemical system is used to measure the amount of electrons resulting from the reaction between the analyte and the reagent system which is proportional to the concentration of the analyte in the blood sample being tested. Those systems which employ an enzyme in the reagent system may be referred to as biosensors since they rely on the interaction of the enzyme (a biological material) with the analyte to provide the detectable response. For example, in the case where glucose is the analyte, the reaction with glucose oxidase and oxygen is represented by equation (A).

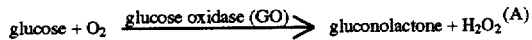

In a colorimetric assay, the released hydrogen peroxide, in the presence of peroxidase, causes a color change in a redox indicator which color change is proportional to the level of glucose in the test fluid. While colorimetric tests can be made semi-quantitative by the use of color charts for comparison of the color change of the redox indicator with the color change obtained using test fluids of known glucose concentration, and can be rendered more highly quantitative by reading the result with a spectrophotometric instrument, the results are generally not as accurate nor are they obtained as quickly as those which can be obtained with the use of a biosensor which relies on an electrochemical response to determine the concentration of the analyte. Aside from its greater accuracy, an electrochemical biosensor generates an electrical signal which can be measured directly thereby facilitating a simplified instrument design. An electrochemical biosensor of this type is more fully described in co-pending application Ser. No. 08/404,303 now U.S. Pat. No. 5,630,986 May 20, 1997 which is incorporated herein by reference.

Referring to the above equation (A), a suitable electrode can measure the formation of $H_2O_2$ by its electrooxidation at the surface of the electrode according to equation (B):

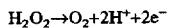

The oxidation current measured at the electrode is directly proportional to the concentration of glucose in the blood sample being tested.

In the initial step of the reaction represented by equation (A), glucose present in the test sample converts the oxidized flavin adenine dinucleotide (FAD) center of the enzyme into its reduced form ($FADH_2$). Because these redox centers are essentially electrically insulated by the enzyme's glycosylated protein shell, direct electron transfer to the surface of a conventional electrode does not occur to any measurable degree in the absence of an unacceptedly high cell voltage. An improvement to this system involves the use of a nonphysiological redox coupling between the electrode and the enzyme to shuttle the electrons between the ($FADH_2$) and the electrode represented by the following scheme in which the redox coupler, typically referred to as a mediator, is represented by M:

*Glucose*+GO(FAD)→*gluconolactone*+GO($FADH_2$)

GO($FADH_2$)+$2M_{ox}$→GO(FAD)+$2M_{red}$+$2H^+$ $2M_{red}$→$2M_{ox}$+$2e^-$ (*at the electrode*)

In this scheme, GO(FAD) represents the oxidized form of glucose oxidase and GO($FADH_2$) indicates its reduced form. The mediating species $M_{ox}$/$M_{red}$ shuttles electrons from the reduced enzyme to the electrode thereby oxidizing the enzyme to cause its regeneration in situ.

Many compounds are useful as mediators due to their ability to accept electrons from the reduced enzyme and transfer them to the electrode. Among the mediators known to be useful as electron transfer agents in analytical determinations are the substituted benzo- and naphthoquinones disclosed in U.S. Pat. No. 4,746,607 (May 24, 1988); the N-oxides, nitroso compounds, hydroxylamines and oxines specifically disclosed in EP 0 354 441 (Feb. 14, 1990); the flavins, phenazines, phenothiazines, indophenols, substituted 1,4-benzoquinones and indamins disclosed in EP 0 330 517 (Aug. 30, 1989) and the phenazinium/phenoxazinium salts described in U.S. Pat. No. 3,791,988 (May 1989). A comprehensive review of electrochemical mediators of biological redox systems can be found in *Analytica Clinica Acta*, 140 (1982), Pp 1–18.

Among the more venerable mediators is hexacyanoferrate, also known as ferricyanide, which is discussed by Schläpfer et al in *Clinica Chimica Acta*., 57 (1974), Pp. 283–289. In U.S. Pat. No. 4,929,545 (May 29, 1990) there is disclosed the use of a soluble ferricyanide compound in combination with a soluble ferric compound in a composition for enzymatically determining an analyte in a sample. Substituting ferricyanide for oxygen in equation (A) provides:

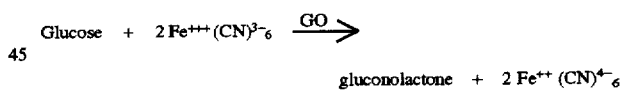

since the ferricyanide is reduced to ferrocyanide by its acceptance of electrons from the glucose oxidase enzyme.

Another way of expressing this reaction is by use of the following set of equations (C):

*Glucose*+GO(FAD)→*Gluconolactone*+GO($FADH_2$)

GO($FADH_2$)+2 Fe($CN_3$)$^{3-}_6$→GO(FAD)+2 Fe(CN)$^{4-}_6$+$2H^+$

2 Fe(CN)$^{4-}_6$→2 Fe(CN)$^{3-}_6$+$2e^-$ (*at the electrode*)

(C)

The electrons released are directly equivalent to the amount of glucose in the blood sample and can be related thereto by measurement of the current which is produced through the fluid upon application of a potential thereto.

As is apparent from the above description, a necessary attribute of a mediator is the ability to remain in the oxidized state under the conditions present on the electrode surface prior to the use of the electrochemical sensor. Any reduction of the mediator will increase the background current resulting in the reading of the sensor being biased. These mediators do tend to be reduced over time, especially under conditions of stress, thereby diminishing the usefulness of the sensors to which they are applied. This reduction of the mediator can be reversed by the application of a positive potential pulse to the electrode bearing the mediator to return at least a portion to its oxidized form. The application of this pulse to the electrode, referred to hereafter as burn-off, provides a current between the electrodes which can be measured. After the burn-off pulse is maintained for a predetermined period of time, usually for a few seconds, the system is switched off to provide an open circuit for a set delay period whereupon the analyte concentration is determined by applying a second potential between the electrodes and measuring the resulting current to provide the read current. This technique is more fully described in co-pending application Serial No. 08/435,993 now U.S. Pat. No. 5,620,579 which is incorporated herein by reference. The dynamic current profile, i.e. the change of current with time, is characteristic for the sensing system and the sample being tested. The ratio of read current to burn current (R/B) provides a way to express the characteristics of the dynamic current profile.

It is necessary that clinical analyses of the type described above are accurate. User control solutions can be used to verify this accuracy by determining whether the testing meter and/or the sensors of the sensing device are working properly. A user control solution is tested for quality control purposes and is not used for calibration. Existing commercial user control solutions include that disclosed in WO 93/21928-A (Published Apr. 24, 1992) which contains water, a predetermined amount of glucose, xanthan, phosphate as a reaction rate regulator and fixed human or bovine red blood cells.

In WO 95/13535, (Published Nov. 12, 1993) there is disclosed a non-serum based control reagent containing water, a predetermined amount of glucose and a dihydroxy alcohol having more than 5 carbon atoms, preferably dipropylene glycol.

There is disclosed in WO 95/13536 (Published Nov. 12, 1993) a serum-free control reagent for glucose determination which comprises a mixture of a predetermined amount of glucose, water, a clay mineral, a buffer, a preservative, a surfactant and a colored or color forming compound.

Although the existing commercial control solutions serve the purpose of checking whether the glucose measuring system is working properly, the meter cannot determine whether the sample tested is a control solution or a true blood sample. This can create a problem with the use of meters having an auto memory function in which the testing results are automatically stored in a memory unit, so that the blood glucose profile over a period of time can be downloaded from the data memory, analyzed and used for medical purposes. Since the system cannot distinguish between the control solution and blood, both values will be recorded in the memory system, and, if not removed, the results from the control solution will skew the glucose profile contained in the memory. This problem can be ameliorated by providing the meter with a mechanism whereby the results obtained using the control solution can be deleted from the memory upon completion of the test. Some commercially available glucose meters provide a manual deletion protocol. However, this manual deletion technique is not fail-safe because of the possibility that the user will forget or neglect to remove the control data from the memory.

It would be desirable and it is an object of the present invention to provide a control solution and a method for testing an amperometric sensing device which automatically allow the sensing device to detect when a control solution rather than blood is being tested.

It is a further object to provide such a method in which the sensing device has a memory system which automatically excludes the data generated using the control solution from the memory unit for blood data.

These objects are achieved by the formulation of a control solution which generates current profiles of the burn-off and the read period which are distinguishable from those which are generated from a blood sample.

SUMMARY OF THE INVENTION

The present invention is an aqueous control solution for testing the performance of an electrochemical sensing device useful for determining the concentration of an analyte in a blood sample. The device comprises a working electrode and a reference electrode. The working electrode has on its surface a composition comprising an enzyme specific for the analyte and a mediator which is a species reduced in response to a reaction between the analyte and the enzyme. The concentration of the analyte is determined as a function of the current which passes through the working electrode. During the operation of the device to determine the concentration of analyte in blood, there is created a dynamic current profile which is measured by a meter in electrical connection with the sensing device.

In order to test the proper functioning of the meter and the sensing device, a control solution, containing a known amount of analyte, can be used. The present invention involves the use of a control solution which is designed to provide a dynamic current profile which is distinctly different from that which would be obtained with blood. When the meter is connected to a memory system which records each separate analysis, the memory system can be designed to accept only those readings which correspond to the dynamic current profile produced by a blood sample and exclude those produced using the control solution. In this manner, the memory system avoids being skewed by the inclusion of readings obtained using the control solution which is not indicative of the analyte level in the blood of the user of the analyte measuring device.

Also included within the scope of the present invention is a method of testing the performance of the electrochemical sensing device using a control solution as described above.

DESCRIPTION OF THE INVENTION

The crux of the present invention is the provision of a control solution which produces a dynamic current profile which can be recognized as different from that of blood by the measuring device's microprocessor and is therefore excludable from the memory system. There are various techniques by which the dynamic current profile produced by the control solution can be altered. For example by adding into the aqueous control solution an organic solvent which is a poor solvent for the redox mediator, the rate of dissolution of the mediator will be decreased, i.e. the concentration of the mediator in the test solution will be decreased in the early stage of the test (the burn period) thereby decreasing the burn current relative to the read current at a given analyte concentration and resulting in a dynamic current profile which is different from that generated by a pure aqueous test sample like blood. Alternatively, the burn current can be reduced by incorporating an oxidizing agent at an adequate concentration in the control solution. When a control solution containing an oxidizing agent is tested, the reduced mediator, upon dissolution, will be oxidized immediately by the oxidizing agent. In other words, the oxidizing agent will short circuit the electrons flowing from the reduced mediator to the surface of the electrode, resulting in a decrease in the burn current. At an adequate concentration, the oxidizing agent will be depleted during the burn period, and the read current will be significantly affected. This again results in a dynamic current profile which is different from that generated by a test sample free of the oxidizing agent.

The characteristics of the dynamic current profile can be expressed in certain ways and the corresponding criteria functions can be set in the microprocessor for the meter to recognize different current profiles and in turn to recognize different samples, control or blood. For example, the rate of change in burn current can be used to express the characteristic or the shape of the dynamic burn current profile. When a blood sample is tested, the chemistry reagent of the sensor is quickly rehydrated and the burn current exhibits a fast monotonic decay after a couple of seconds into the test, so that the rate of change in the burn current is high and it bears a negative sign. However, when the test sample is a control solution, either containing an organic solvent or an oxidizing agent, not only the burn current is decreased creased but the rate of change in the burn current is also altered to show a slow increase, i.e. the rate of change in the burn current is low and it bears a positive sign for a control solution. Therefore, the rate of change in the burn current can be set as a criterion function: when the rate of change in the burn current is high and bears a negative sign, the sample tested is blood; when the rate of change in the burn current is low and bears a positive sign, the sample tested is a control solution. Alternatively, it is possible to use the ratio of the read current to the burn current (R/B) to express the difference in the dynamic current profiles for a blood sample and a control solution. As discussed above, the burn current is decreased by the addition of an organic solvent or an oxidizing agent to the control solution while the read current is not significantly affected; accordingly the R/B ratio is greater for a control solution than for a blood sample. A R/B function can be set as the criterion: when R/B is greater than a certain value, the test material is a control solution; when R/B is smaller than that value, the test material is a blood sample.

In a preferred embodiment of the present invention, the dynamic current profile of the sensor is determined by applying an initial potential across the electrodes of the sensing device to oxidize at least a portion of the mediator which has undergone reduction and measuring the current which flows between the electrodes to provide a burn current. At this point the system is switched to an open circuit, i.e. the potential applied to the electrodes is terminated and the output impedance of the electronic circuit on the two electrodes of the sensor is infinitely high for a set delay period after which the concentration of the analyte is determined by applying a second potential between the electrodes and measuring the current which flows between them to provide a read current. The characteristic of the dynamic current profile can be expressed by the ratio of the read current to the burn current.

The control solution is a water based composition which contains four basic elements. They are:

a) a polymeric material which mimics the fluid mechanics of blood, i.e. exhibits the viscosity and diffusional behavior of electrolytes in blood. Suitable polymers include polyethylene oxide, polyhydroxyethyl methacrylate and polyvinyl pyrolidone. Typically, the control solution will contain from 12 to 20% (w/v) of one or more of these polymeric ingredients.

The second basic ingredient is a predetermined amount of the analyte. The concentration of the analyte is not critical so long as it falls within the concentration limits which the analyzer is capable of detecting. Various analytes can be measured by the type of analyzer under consideration, e.g. cholesterol, alcohol, glutamate, lactate and glucose provided that the appropriate enzymes are applied to the working electrode. In the case of a sensing device for the determination of glucose in which the enzyme is glucose oxidase, the concentration of glucose in the control solution will typically range from 30 to 400 mg/dL.

The control solution is buffered to a pH in the range of from 4.8 to 7.5 for the optimum and reproducible performance of the sensor. The particular buffer employed is not critical; preferred buffers include citric acid/sodium citrate, phosphoric acid or sodium phosphate in sufficient quantity to maintain the control solution's pH within the desired range.

Finally, there is included in the control solution a material which affects the sensor in a manner which causes it to provide a dynamic current profile which is distinctly different than that of blood without substantially affecting the sensor's enzyme. One way to express the characteristic of the dynamic current profile is to use the ratio of the read current to the burn current (R/B). By programming the analyzer's microprocessor to accept only those results whose R/B ratios conform to a pre-set range, those tests which provide a R/B ratio outside that range are automatically excluded. The dynamic current profile of a test using the sensor as previously described is most conveniently altered by adding an ingredient to the control solution which affects the function of the mediator. For example, ethylene glycol can be added to the control solution to cause the solution to dissolve the mediator more slowly than would be the case if the control solution were totally an aqueous based system. Thus, in the case where ferricyanide is the mediator, the addition of 15 to 50% (w/v) ethylene glycol will slow the dissolution of mediator sufficiently to provide a control solution with dynamic current profile (thus an R/B ratio) sufficiently distinct from that obtained using blood for the microprocessor to recognize it as non-blood sample and not enter it into the memory. The slowing of the dissolution rate of the mediator causes the increase in the R/B ratio since the burn current is decreased to a much greater degree that the read current. Examples of other additives which can be added to the control solution to slow down the dissolution rate of the mediator include N-methylpyrrolidone and N-propanol. All additives to the control solution must, of course, be compatible with the enzyme present in the reagent.

Additives can be added to the control solution to change its dynamic current profile by means other than slowing the dissolution rate of the mediator. For example, an oxidizing agent can be added to partially oxidize the mediator. This will affect the dynamic current profile by decreasing the burn current due to the short circuit of the electrons flowing from the reduced mediator to the electrode. Suitable oxidizing agents include potassium permanganate, potassium perchromate, potassium dichromate, sodium perchlorate and sodium periodate. By selecting a suitable concentration of oxidizing agent, it will be depleted during the burn period, and the read current will not be significantly affected. Thus, the R/B ratio will be increased for the control.

The method of practicing the present invention is further illustrated by the following example:

EXAMPLE I

A. (Formulating the Control Solution)

The control stock, containing everything but glucose in the control solution, was made in two main steps:

i) making the PVP stock (polyvinyl pyrrolidone solution in citrate buffer). The composition of the PVP stock is given in Table 1.

TABLE 1

| Ingredient | quantity, gram/liter |
| --- | --- |
| PVP | 220 |
| Sodium borohydride | 0.969 |
| Citric acid | 9.83 |
| Sodium citrate | 28.00 |
| Sodium benzoate | 2.00 |
| DI water | q.s. to 1 L |

The PVP was added very slowly to water, with vigorous stirring, until dissolved. Sodium borohydrate was then added slowly with gentle stirring to reduce the oxidizing impurities possibly carried over from the polymerization process. Upon completion of the reaction, citric acid was added to bring the pH down in order to decompose any unreacted borohydride. Finally, sodium citrate was added to bring the pH to the desired level of 5.0.

ii) adding ethylene glycol and red dye to the PVP stock. The control stock was made by mixing 75 parts (by volume) of PVP stock with 25 parts of ethylene glycol. FD&C Red Dye #40 is added to a concentration of 0.4 g per liter of control stock to give the control solution a deep red color which mimics blood in appearance. Glucose was added to the control solution at three levels:

Low: 97 mg/dL
Normal: 152 mg/dL
High: 371 mg/dL

B. (Testing With a Blood Sample and With a Control Solution)

With the meter turned on and a sensor in the sensing position, i.e. the contact pads on the electrodes of the sensor are in contact with the electronic circuit of the meter, the electrodes were subjected to a potential of 0.4 volts. The sample (blood or control solution) was applied to the sensor whose working electrode carried glucose oxidase and ferricyanide which, in the presence of glucose, enter into the previously described electrochemical reaction to provide electrons. Upon being wetted by the sample, the meter detects a current spike and starts the timing for the test which lasts 30 seconds, the first 10 seconds of which is the burn period. At the $10^{th}$ second of the test, the burn current was recorded ($i_{burn}$) and the potential applied to the electrodes terminated leaving an open circuit between the electrodes. The open circuit condition, referred to as the "waiting period", was maintained for 10 seconds to allow the reaction between the glucose and reagent to proceed. At the $20^{th}$ second of the test, a potential of 0.4 volts was again applied to the electrodes to start the 10 second read period. At the $30^{th}$ second of the test the read current ($i_{read}$) was recorded and the potential applied to the electrodes terminated. This completed the test. FIG. 1 depicts the current profiles for blood (WB) and control testing. The recorded currents were:

WB: $i_{burn} = 1586$ (nA)   $i_{read} = 1127$ (nA)

Control: $i_{burn} = 865$ (nA)   $i_{read} = 955$ (nA)

C. (Detecting a Control Sample by the Meter)

From FIG. 1 it can be seen that the dynamic current profile obtained with the control solution is distinctly different from that obtained with blood. The burn current shows a monotonic slow increase with time for the control, while for the blood sample the burn current, except at the very beginning of the test, shows a fast decay with time. Using the ratio of read current to the burn current one can quantify the difference in current profiles.

At the completion of the test, the microprocessor in the meter calculates the glucose value according to equation (1).

$$G = (i_{read} - 370.73)/9.33 \text{ mg/dL}$$

(1) and calculates the ratio of the read current to the burn current according to equation (2):

$$R/B = i_{read}/i_{burn}$$

(2)

The criterion function of the ratio of the read current to the burn current stored in the microprocessor is:

if $G \leq 150$ and if $R/B > 0.75 + 0.001 * G$ then: The sample is control solution, exclude the data from the memory unit for blood wherein "if . . . then" is a logic function which enables the microprocessor to make a choice according to the result of the comparison set by that logic function.

else: The sample is blood, input the data into the memory unit for blood.

else:

if $G > 150$ and if $R/B > 0.8625 + 0.00025 * G$ then: The sample is control solution, exclude the data from the memory unit for blood.

else: The sample is control solution, input the data into the memory unit for blood.

The G and R/B values from the tests illustrated by FIG. 1 are:

WB:   $G = (1127 - 370.73)/9.33 = 81$ mg/dL $R/B = 1127/1586 = 0.711 < 0.75 + 0.001 * 81 = 0.831$

Control:   $G = (955 - 370.73)/9.33 = 63$ mg/dL $R/B = 955/865 = 1.104 > 0.75 + 0.001 * 63 = 0.813$ Upon checking the data obtained from the blood and the control tests against the criterion function, the samples are determined as blood and control by the microprocessor, respectively, and the control data is excluded from the memory unit for blood.

What is claimed is:

1. An aqueous control solution for testing the performance of an electrochemical sensing device useful for determining the concentration of an analyte in a blood sample which device comprises a working electrode and a reference electrode which working electrode has on its surface a composition comprising an enzyme specific for the analyte, a mediator which is a species reduced in response to a reaction between the analyte and the enzyme, and wherein the concentration of the analyte in the fluid test sample is determined as a function of the current measured which passes the working electrode which control solution provides a dynamic current which is distinctly different from the dynamic current profile which would be obtained in the electrochemical sensor with blood.

2. The control solution of claim 1 which comprises:
   a) a polymeric material which mimics the fluid mechanics of blood;
   b) a predetermined amount of the analyte;
   c) a buffering system capable of maintaining the solution's pH at a range of from about 4.8 to about 7.5;
   d) a material which affects the sensor in a manner that causes the control solution to provide a dynamic current profile distinctly different than that of blood without substantially affecting the function of the enzyme; and
   e) water.

3. The control solution of claim 2 wherein the polymeric material which mimics the fluid dynamics of blood is polyethylene oxide, polyhydroxyethyl methacrylate and polyvinyl pyrrolidone.

4. The control solution of claim 2 wherein the buffering system is comprised of citric acid/sodium citrate, phosphoric acid or sodium phosphate.

5. The control solution of claim 2 wherein the material which affects the sensor affects the mediator.

6. The control solution of claim 5 wherein the material that affects the mediator to cause a current profile different than blood is an organic solvent which results in slower dissolution and/or diffusion of the mediator when the control solution is applied to the sensor than is the case with blood.

7. The control solution of claim 5 wherein the mediator is a ferricyanide and the solvent is ethylene glycol, N-methylpyrrolidone or N-propanol.

8. The control solution of claim 1 wherein the dynamic current profile is determined by applying an initial potential across the electrodes to oxidize at least a portion of the mediator which has undergone reduction and measuring the current which flows between the electrodes to provide a burn current, switching the system to an open circuit for a set delay period and then determining the concentration of the analyte by applying a second potential between the electrodes and measuring the current which flows therebetween to provide a read current and the dynamic current profile is the ratio of read current to burn current.

9. The control solution of claim 6 wherein the material which causes the current profile different from that of blood is an oxidizing agent.

10. The control solution of claim 9 wherein the oxidizing agent is potassium permanganate, potassium perchromate, potassium dichromate, sodium perchlorate or sodium periodate.

11. A method for testing the performance of an electrochemical sensing device for determining the concentration of an analyte in a blood sample which device comprises a meter and electrochemical sensing means wherein the method comprises the steps of:
   a) providing the electrochemical sensing device having a sensing means which includes a working electrode and a reference electrode which working electrode has on its surface a composition comprising an enzyme specific for the analyte and a partially reduced mediator which is a species reduced in response to a reaction between the analyte and the enzyme;
   b) placing a control solution between the working electrode and the reference electrode of the sensing means which control solution is capable of electrically connecting these electrodes and which control solution contains a known concentration of the analyte and provides a dynamic current profile which is distinctly different than that which is provided by a blood sample under similar conditions;
   c) applying a potential between the electrodes to return at least a portion of the mediator back to its oxidized form to provide a measurable burn current which current is measured;
   d) terminating the potential applied to the electrodes to provide an open circuit for a set delay period;
   e) applying a second voltage between the electrodes and measuring the current in the control solution to provide a read current and measuring the read current; and
   f) determining the dynamic current profile of the control solution in terms of the ratio of read current to burn current which dynamic current profile is distinctly different from the dynamic current profile which would be obtained with a blood sample.

12. The method of claim 11 wherein the control solution comprises:
   a) a polymeric material which mimics the fluid mechanics of blood;
   b) a predetermined amount of the analyte;
   c) a buffering system capable of maintaining the control solution's pH at a range of from about 4.8 to about 7.5;
   d) a material which affects the sensor in a manner that causes the control solution to provide a dynamic current profile which is distinctly different than that of blood without substantially affecting the function of the enzyme; and
   e) water.

13. The method of claim 11 wherein the control solution provides a distinctly different dynamic profile by affecting the mediator.

14. The method of claim 13 wherein the material that affects the mediator is an organic solvent which results in slower dissolution and/or diffusion of the mediator than would be the case if blood rather than the control solution were applied to the sensing means.

15. The method of claim 14 wherein the mediator is ferricyanide and the solvent is ethylene glycol, N-methylpyrrolidone or N-propanol.

16. The method of claim 11 wherein the material that affects the mediator is an oxidizing agent.

17. The method of claim 16 wherein the oxidizing agent is potassium permanganate, potassium perchromate, potassium dichromate, sodium perchlorate or sodium periodate.

18. The method of claim 11 wherein the electrochemical sensing device has a microprocessor and a memory unit for maintaining test results and wherein the microprocessor contains a range of ratios of the read current to the burn current, which range corresponds to that which would be obtained with blood, which microprocessor will exclude the testing result from being stored in the memory unit when the current profile in terms of the ratio of the read current to burn current obtained from the test is determined to be for a control solution upon comparing it to the range of ratios of read current to burn current for blood stored within the microprocessor.

* * * * *